United States Patent [19]
Lax et al.

[11] Patent Number: 5,741,225
[45] Date of Patent: Apr. 21, 1998

[54] METHOD FOR TREATING THE PROSTATE

[75] Inventors: Ronald G. Lax, Grass Valley; Stuart D. Edwards, Los Altos; Hugh R. Sharkey, Redwood Shores, all of Calif.

[73] Assignee: Rita Medical Systems, Mountain View, Calif.

[21] Appl. No.: 589,111

[22] Filed: Jan. 23, 1996

Related U.S. Application Data

[63] Continuation-in-part of Ser. No. 148,441, Nov. 8, 1993, Pat. No. 5,486,161, which is a continuation-in-part of Ser. No. 929,638, Aug. 12, 1992, abandoned, Ser. No. 12,370, Feb. 2, 1993, Pat. No. 5,370,675, Ser. No. 62,364, May 13, 1993, Pat. No. 5,435,805, Ser. No. 61,647, May 13, 1993, Pat. No. 5,421,819, and Ser. No. 61,072, May 14, 1993, abandoned.

[51] Int. Cl.$^6$ ..................................................... A61B 17/39
[52] U.S. Cl. .................................................................. 604/22
[58] Field of Search ................................... 604/19–22, 53, 604/164, 280; 606/39, 45, 32; 607/96, 98, 99–102, 113, 115, 116, 138, 156; 601/2

[56] References Cited

U.S. PATENT DOCUMENTS 5,421,819  6/1995  Edwards et al. ........................... 604/22

*Primary Examiner*—Manuel Mendez
*Attorney, Agent, or Firm*—Wilson Sonsini Goodrich & Rosati

[57] ABSTRACT

A method of medical treatment of the prostate provides an ablation apparatus. The ablation apparatus includes a cannula, an electrode at least partially positioned in the cannula, and an insulation sleeve positioned in a surrounding relationship to at least a portion of the electrode. A distal end of the cannula is positioned in a rectum of a patient. The distal end of the cannula is advanced through a rectal wall of the rectum. A distal end of the electrode if advanced from the cannula into the prostate. Electromagnetic energy is delivered from the electrode to the prostate and an ablation zone is created in the prostate.

19 Claims, 7 Drawing Sheets

5,741,225

METHOD FOR TREATING THE PROSTATE

RELATIONSHIP TO COPENDING APPLICATIONS

This application is a continuation-in-part of application Ser. No. 08/148,441 filed Nov. 8, 1993 now U.S. Pat. No. 5,486,161; which is a CIP of Ser. No. 07/929,638 filed Aug. 12, 1992, now abandoned; Ser. No. 08/012,370 filed Feb. 2, 1993 now U.S. Pat. No. 5,370,675; Ser. No. 08/062,364 filed May 13, 1993 now U.S. Pat. No. 5,435,805, Ser. No. 08/061,647 filed May 13, 1993 now U.S. Pat. No. 5,421,819; AND Ser. No. 08/061,072 filed May 14, 1993, now abandoned; the entire contents of each of the above applications being hereby incorporated by reference.

FIELD OF THE INVENTION

This invention is directed to a method for treating a selected tissue site, and more particularly to a method for creating an ablation in a prostate utilizing an ablation apparatus that pierces the rectal wall.

BACKGROUND OF THE INVENTION

Treatment of cellular tissues usually requires direct contact of target tissue with a medical instrument, usually by surgical procedures exposing both the target and intervening tissue to substantial trauma. Often, precise placement of a treatment probe is difficult because of the location of a target tissue in the body or the proximity of the target tissue to easily damaged, critical body organs, nerves, or other components.

High frequency currents are used in electrocautery procedures for cutting human tissue especially when a bloodless incision is desired or when the operating site is not accessible with a normal scalpel but presents an access for a thin instrument through natural body openings such as the esophagus, intestines or urethra. Examples include the removal of prostatic adenomas, bladder tumors or intestinal polyps. In such cases, the high-frequency current is fed by a surgical probe into the tissue to be cut. The resulting dissipated heat causes boiling and vaporization of the cell fluid at this point, whereupon the cell walls rupture and the tissue is separated. The frequency of the current for this use must be above ca. 300 kHz in order to avoid any adverse such as nerve and/or muscle responses.

Destruction of cellular tissues in situ has been used in the treatment of many diseases and medical conditions alone or as an adjunct to surgical removal procedures. It is often less traumatic than surgical procedures and may be the only alternative where other procedures are unsafe. Ablative treatment devices have the advantage of using a destructive energy which is rapidly dissipated and reduced to a non-destructive level by conduction and convection forces of circulating fluids and other natural body processes.

Microwave, radio frequency, acoustical (ultrasound) and light energy (laser) devices, and tissue destructive substances have been used to destroy malignant, benign and other types of cells and tissues from a wide variety of anatomic sites and organs. Tissues treated include isolated carcinoma masses and, more specifically, organs such as the prostate, glandular and stromal nodules characteristic of benign prostate hyperplasia. These devices typically include a catheter or cannula which is used to carry a radio frequency electrode or microwave antenna through a duct to the zone of treatment and apply energy diffusely through the duct wall into the surrounding tissue in all directions. Severe trauma is often sustained by the duct wall during this cellular destruction process, and some devices combine cooling systems with microwave antennas to reduce trauma to the ductal wall. For treating the prostate with these devices, for example, heat energy is delivered through the walls of the urethra into the surrounding prostate cells in an effort to kill the tissue constricting the urethra. Light energy, typically from a laser, is delivered to prostate tissue target sites by "burning through" the wall of the urethra. Healthy cells of the duct wall and healthy tissue between the nodules and cut wall are also indiscriminately destroyed in the process and can cause unnecessary loss of some prostate function. Furthermore, the added cooling function of some microwave devices complicates the apparatus and requires that the device be sufficiently large to accommodate this cooling system.

OBJECTS AND SUMMARY OF THE INVENTION

Accordingly, an object of the invention is to provide an RF medical ablation device which can be deployed in the body for the purpose of ablation of difficult to access tissues.

Another object of the invention is to provide an RF medical ablation device which can be deployed in a non-linear path through body components and tissue to reduce the mass of specifically difficult to access tissues.

A further object of the invention is to provide a method for treatment of the prostate.

These and other objects of the invention are achieved in a method of medical treatment of the prostate. An ablation apparatus is provided. The ablation apparatus includes a cannula, an electrode at least partially positioned in the cannula, and an insulation sleeve positioned in a surrounding relationship to at least a portion of the electrode. A distal end of the cannula is positioned in a rectum of a patient. The distal end of the cannula is advanced through a rectal wall of the rectum. A distal end of the electrode if advanced from the cannula into the prostate. Electromagnetic energy is delivered from the electrode to the prostate and an ablation zone is created in the prostate.

The tube can have an optical viewing device associated therewith for examining tissue adjacent its distal end and can be a hollow needle, laparoscope, cystoscope, and the like. The electrode can also be a hollow tube, the proximal end thereof being adapted to be connected to a suction source for aspiration of tissue adjacent its distal end or it can optionally contain a fiber optic, the end thereof being enclosed within the tube and closely adjacent its distal end. In one embodiment, the electrode is a hollow electrode tube of highly flexible memory metal, preformed to have a curved memory configuration. The portion of the electrode tube an its surrounding sleeve extending beyond the distal end of the outer tube adopts the curved memory configuration, causing it to follow a curved path when extended through intervening tissue to reach a target tissue to be ablated.

In one embodiment for ablation of difficult to access tissues, the curved memory configuration is predetermined to correspond to a curved, tortuous path from the point of entry in the body, between and around obstacles or sensitive tissue to the area to be ablated, whereby the electrode can reach the difficult to access tissue for ablation.

In one embodiment, the electrode is hollow and contains a fiber optic for examining tissue adjacent its distal end, the end of the fiber optic being enclosed within the tube and closely adjacent its distal end.

A method of this invention for medical ablation of difficult to access tissues comprises the following steps. A hollow needle is inserted through a tissue layer, the needle enclosing a conductive electrode of highly flexible memory metal having predetermined curved memory configuration and a sharpened distal terminus, the electrode being enclosed within an insulating sleeve axially moveable thereon and bendable therewith. Then the electrode and sleeve is advanced from the terminal end of the hollow needle, whereby the portion of the electrode and sleeve advanced beyond the end of the needle adopt the predetermined curved memory configuration, and the electrode and sleeve follow a correspondingly predetermined curved path through tissue to the site to be ablated. Then a portion of the sleeve is withdrawn from the terminus of the electrode to expose a predetermined electrode area required for ablation. RF energy is then applied to the tissue surrounding the exposed electrode area to effect ablation thereof.

In one embodiment, the medical ablation device of 1 includes a punch means connected to the stylet for thrusting the stylet through intervening tissue to the tissue to be treated.

DETAILED DESCRIPTION OF THE INVENTION

The medical ablation devices of this invention are uniquely superior for localized therapeutic ablation to remove or reduce undesired tissue masses from remote locations in the body. With a suitably shaped rigid or flexible delivery tube, the devices can be used with conventional delivery systems including scopes such as laparoscopes, cystoscopes, and the like. With delivery tubes such as needles, the device with a memory shaped electrode can be used to ablate undesired tissue in orthopedic, neurological, gynecological and for less invasive surgical applications such as near zero surgical ablation of spinal discs to alleviate encroachment and pressure from herniated disks on adjacent nerves in the spinal column.

Figure 1:
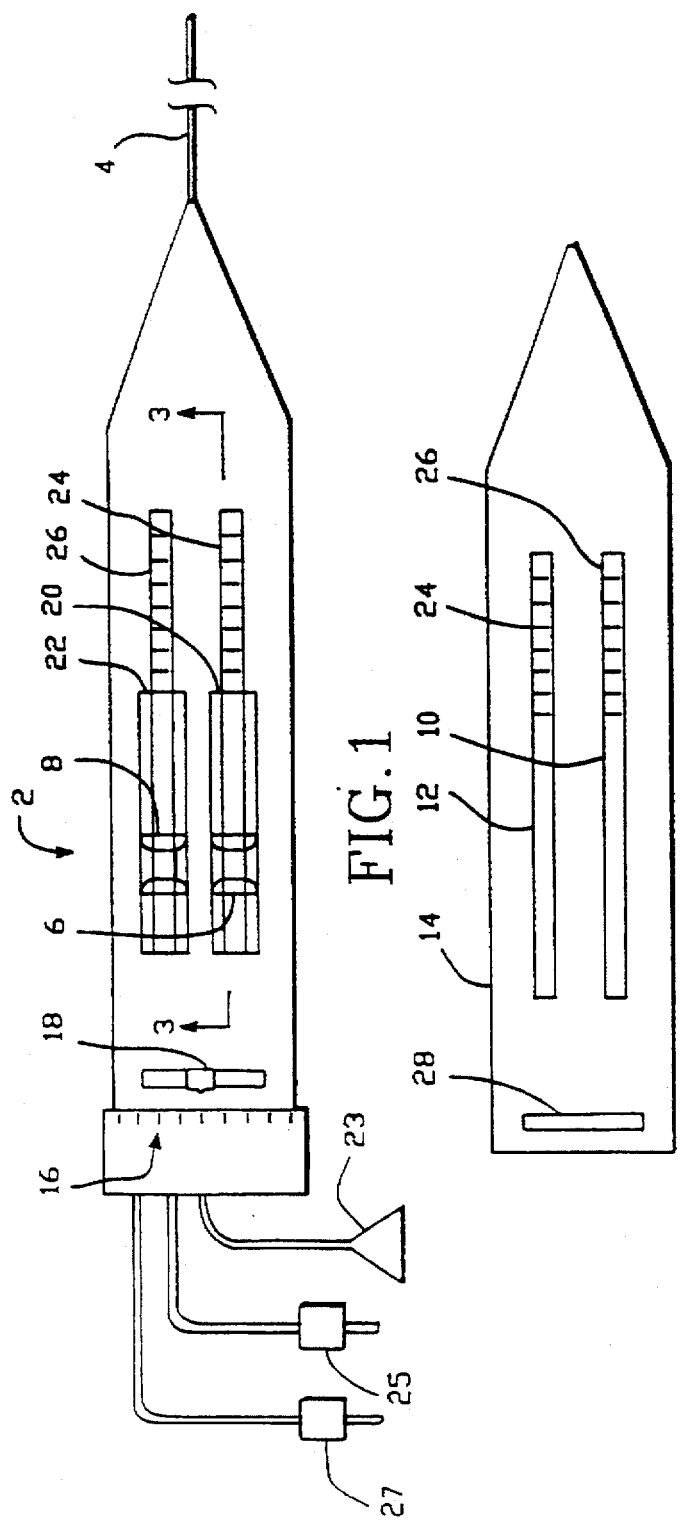
FIG. 1 is a planar view of a stylet ablation device of this invention.
Figure 2:
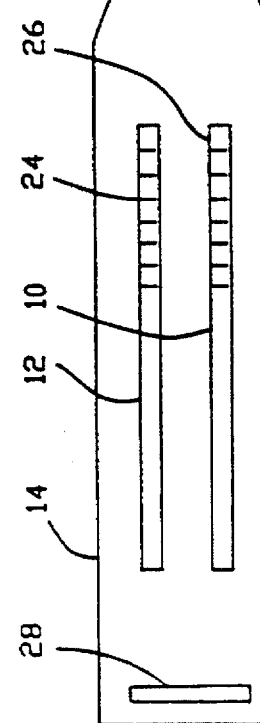
FIG. 2 is a top view of the handle top plate of the stylet ablation device shown in FIG. 1.

Referring to the drawings, FIG. 1 is a planar view of a stylet ablation device of this invention. The device comprises a handle portion 2 and a delivery tube portion 4. Stylet sleeve control manual tab 5 and stylet electrode control manual tab 8 are mounted for sliding engagement in slots 10 and 12 in the handle top plate 14 (FIG. 2). Index markings 16 indicate the relative angle of orientation of the stylet with respect to the stylet angle indicator 18. Angle indicator 18 can be a bubble in a curved transparent tube, a weighted pivot dial indicator or an electronic angle indicator. The position of the distal edges 20 and 22 of the tab slides 5 and 8 with their respective gauge reference strips 24 and 26 independently indicate the relative advancement and retraction of the stylet electrode and sleeve shown in FIGS. 2–4.

Connectors for the fiber optic connector 23, RF power connector 25, and ohmic resistance detector 27 extend from the proximal end of the handle housing.

FIG. 2 is a top view of the handle top plate of the stylet ablation device shown in FIG. 1. Slots 10 and 12 receive the respective tabs 6 and 8 for sliding engagement therein. Slot 28 receives the stylet angle indicator.

Figure 3:
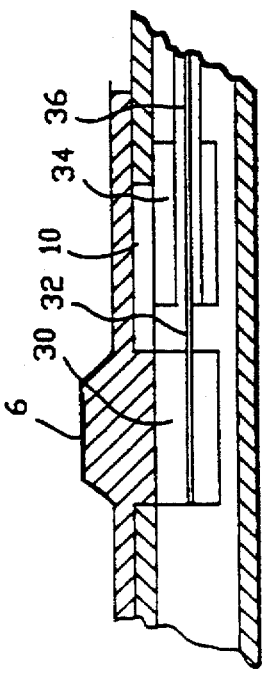
FIG. 3 is a fragmentary cross-sectional view of the manual control portion of the handle of the stylet ablation device shown in FIG. 1, taken along the line A—A in FIG. 1.

FIG. 3 is a fragmentary cross-sectional view of the manual control portion of the handle of the stylet ablation device shown in FIG. 1, taken along the line A—A. Manual electrode tab 6 is attached to an electrode connector 30 which is connected to the proximal end of the stylet electrode 32. Manual sleeve table 8 (FIG. 1) is connected to a sleeve connector 34 which is connected to the proximal end of the sleeve 36.

The electrode 32 is preferably made of a flexible, shape memory metal such as nickel-titanium allow or tempered steel. The sleeve is made of a highly conformable insulating plastic material such as polyamide.

Simultaneous forward and rearward movement of the control tabs 6 and 8 effect simultaneous advancement and retraction f the treatment stylet. Individual movement of the control tabs 6 and 8 provide individual advancing and retracting movement of the respective sleeve and electrode. Indexing strips 24 and 26 provide reference points for controlled positioning of the sleeve control tabs 6 and 8, permitting precise, independent positioning of the stylet elements for controlled ablation of remote body portions as is explained in greater detail hereinafter.

Figure 4:
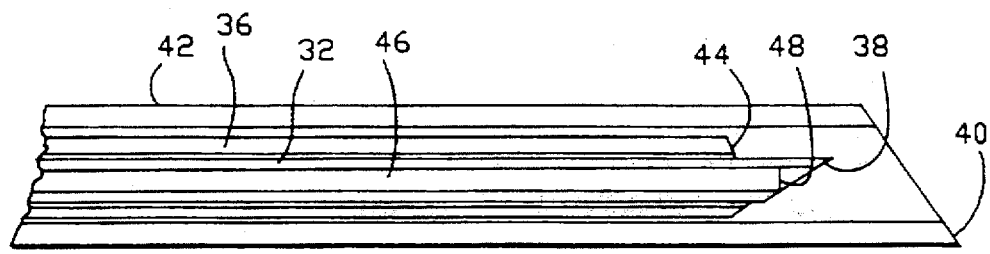
FIG. 4 is a fragmentary cross-sectional view of the tip of the stylet ablation device such as that shown in FIG. 1 with the stylet retracted into the tip.

FIG. 4 is a cross-sectional view of the tip of the stylet ablation device such as that shown in FIG. 1 with the stylet retracted into the tip for initial insertion to a position accessible with a straight needle. The electrode tip 38 is positioned behind the leading sharpened tip 40 of the needle or tube 42. The insulating sleeve tip 44 is positioned just behind the leading edge of the electrode tip 38.

When the electrode 32 is a hollow tube, it can be a conduit for aspiration during treatment, liquid delivery, or in the embodiment shown, a housing for a fiber optic 46. The polished fiber optic tip 48 is then positioned behind the electrode tip 38 to facilitate viewing of the tissue surrounding the electrode tip during insertion.

Figure 5:
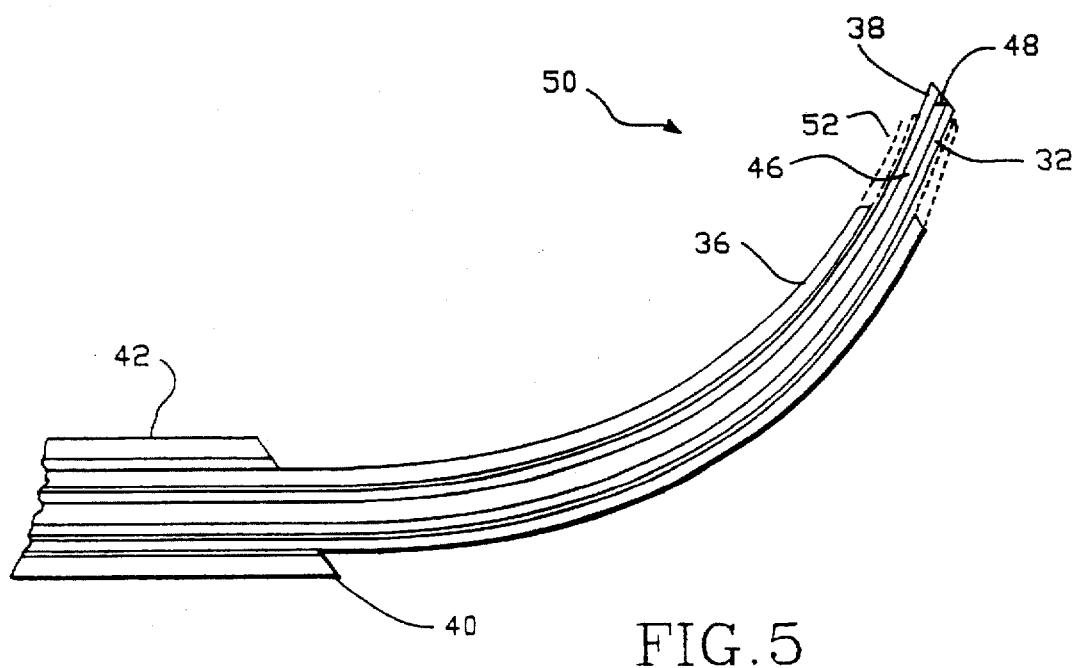
FIG. 5 is a fragmentary cross-sectional view of the tip of the stylet ablation device shown in FIG. 3 with a flexible stylet having a predetermined curved configuration, with the electrode and sleeve extended from the tip.

FIG. 5 is a cross-sectional view of the tip of the stylet ablation device shown in FIG. 4 with the electrode and sleeve extended. This embodiment shows a flexible stylet 50 having a predetermined curved configuration. The flexible stylet can also be straight, if the remote position can be reached by a straight path from the point of entry without damaging a vital body component. The electrode can be made of a shape memory alloy, shaped to revert to a desired configuration when released from the tubing. The configuration can be simple curves, a combination of straight portions and curves, curves with differing radii, in two or three dimensions, selected to direct the electrode and its surrounding flexible, highly conformable sleeve in a preselected two or three dimensional path through tissue to a site to be ablated.

Methods for shaping shape memory alloys are well known in the art and are not a part of this invention. In general, the alloys are annealed with heat and then set in the desired memory shape by quick cooling the annealed electrode while maintaining it in the non-linear shape ultimately desired.

The sleeve 36 is initially in the dotted line position 52. Following insertion into the body to the specific site to be ablated, the sleeve 36 is withdrawn from a selected portion of the electrode 32 to the solid line position to expose the specific electrode area required to form a lesion of the desired size.

A method of this invention for medical ablation of difficult to access tissues comprising first inserting a hollow needle through a tissue layer, the needle enclosing a conductive electrode of highly flexible memory metal having a predetermined curved memory configuration and a sharpened distal terminus, the electrode tube being enclosed within an insulating sleeve axially moveable thereon and bendable therewith. Then the electrode and sleeve are advanced from the terminal end of the hollow needle, whereby the portion of the electrode and sleeve advanced beyond the end of the needle adopt the predetermined curved memory configuration and the electrode and sleeve follow a correspondingly predetermined curved path through tissue to the site to be ablated. Then a portion of the sleeve is withdrawn from the terminus of the electrode to expose a predetermined electrode area for ablation. Finally, RF energy is applied to the tissue surrounding the exposed electrode area to effect ablation thereof.

Figure 6:
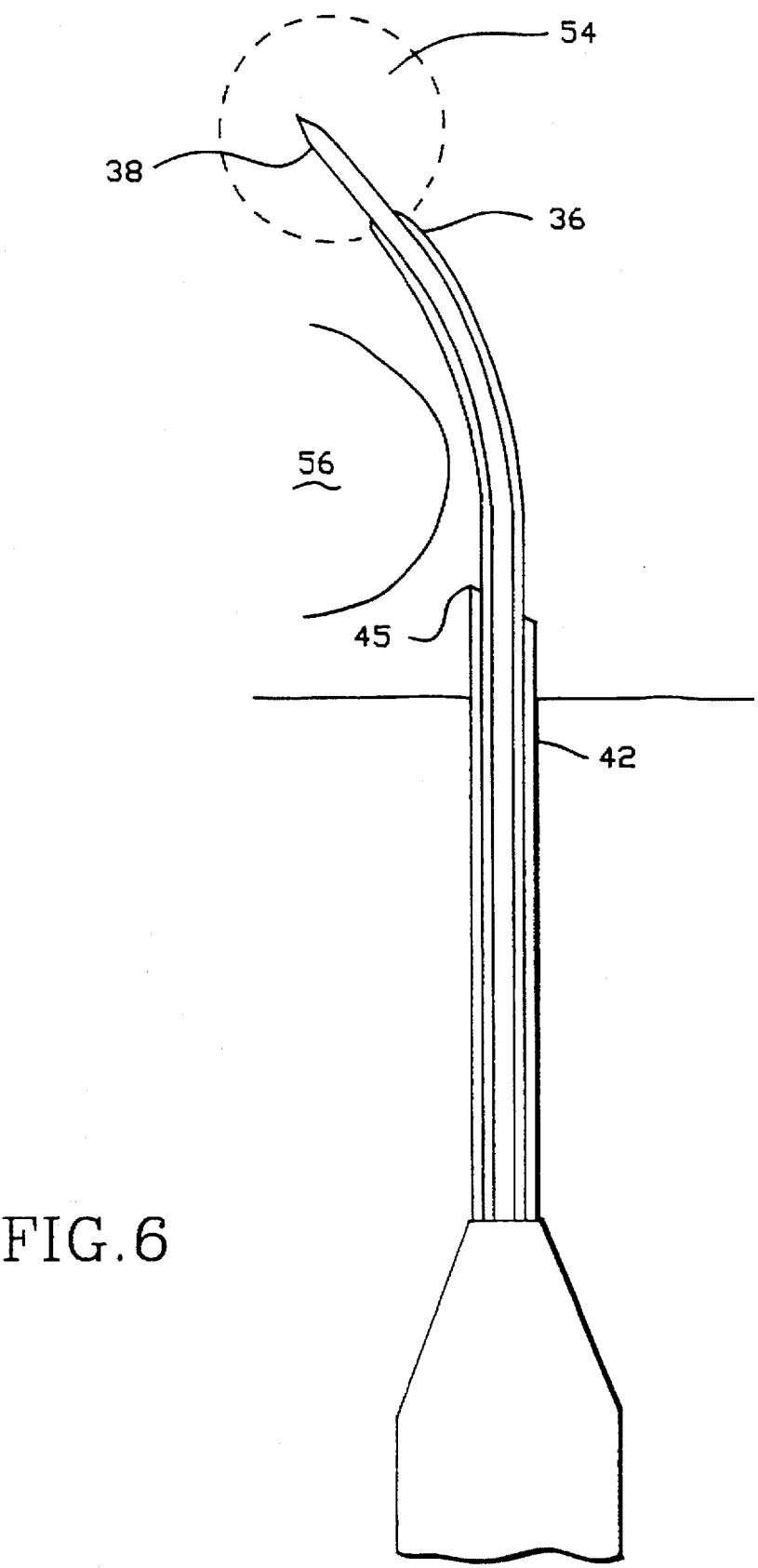
FIG. 6 is a schematic view showing use of an embodiment with a shape memory electrode preformed into a curved shape to treat a near zero access area behind an obstruction.

Referring to FIG. 6, use of an embodiment with a shape memory electrode preformed into a curved shape to ablate a near zero access area behind an obstruction in the body. The objective of the treatment is to reduce the size of the mass 54 behind a rigid obstacle such as bone 56 (or area to be protected from penetration). The electrical conductor and sleeve is extended from the needle 40 through surrounding tissue around the obstacle to its back surface, and the target tissue to be reduced. The sleeve 36 is then withdrawn to a position exposing the electrode area required to ablate the tissue mass. Heat is generated in the target tissue from an electric current or electromagnetic field produced by the electrical conductor. Preferably, the volume of tissue being treated is controlled by moving the non-conductive sleeve to expose a selected length of electrode in the body tissue to be treated, the remaining area of the electrode remaining shielded by the sleeve to protect the intervening tissues. The amount and duration of the energy delivery is also varied to control the volume of tissue being treated. The current passes to a large surface area grounding plate contacting the outer skin surface.

Figure 7:
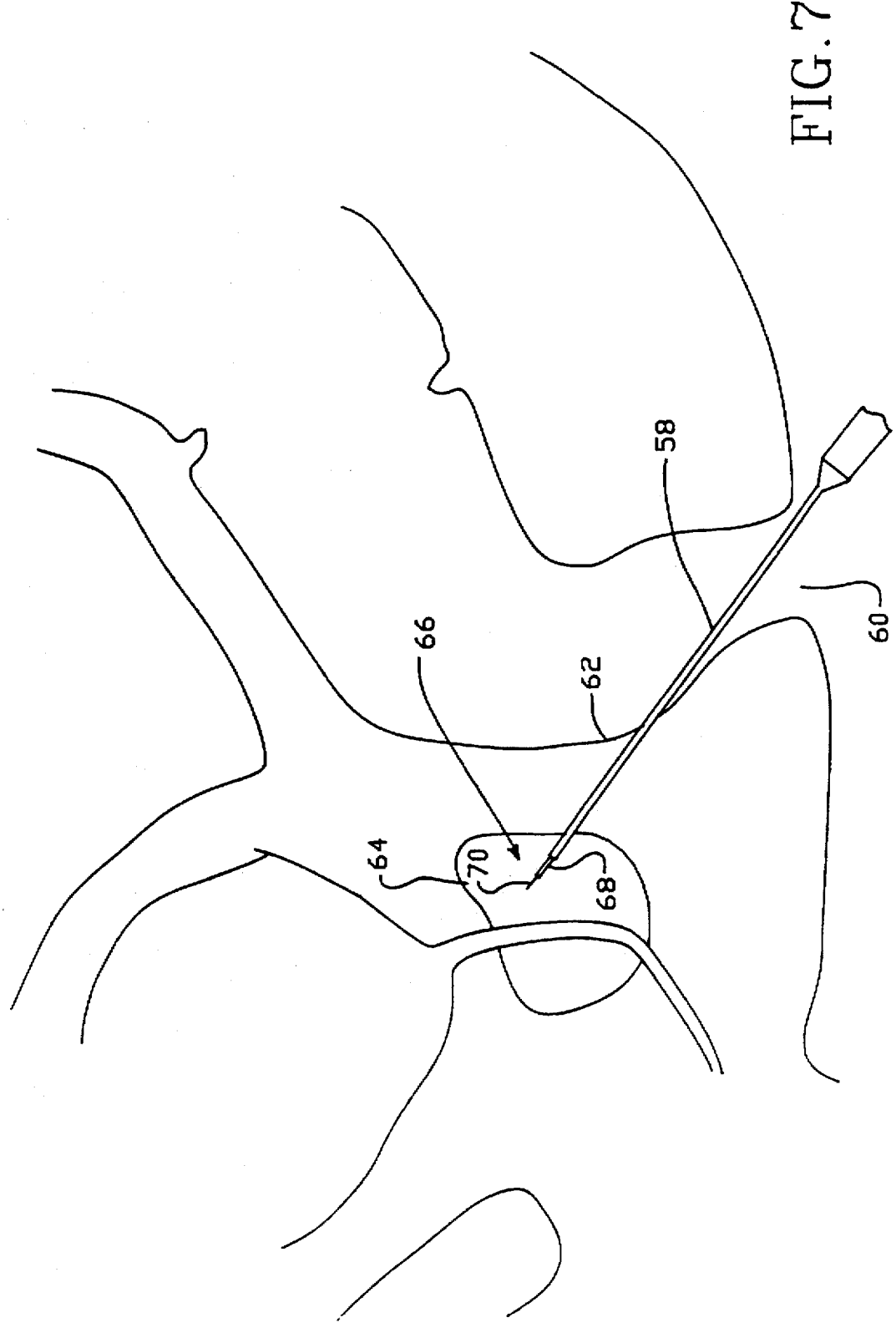
FIG. 7 is a schematic view showing use of a device of this invention for rectal ablation of the prostate.

FIG. 7 is a schematic view showing use of a device of this invention for rectal ablation of the prostate. The sharp tipped cannula 58 is inserted into the rectum 60 and through the rectal surface 62 to the prostate 64. The stylet 66 is extended to the area of the prostate to be ablated. The sleeve 68 is then withdrawn, exposing the electrode 70, and RF power is applied to effect the ablation, the current passing from the electrode 70 through the surrounding tissue to a conventional surface electrode (not shown).

Figure 8:
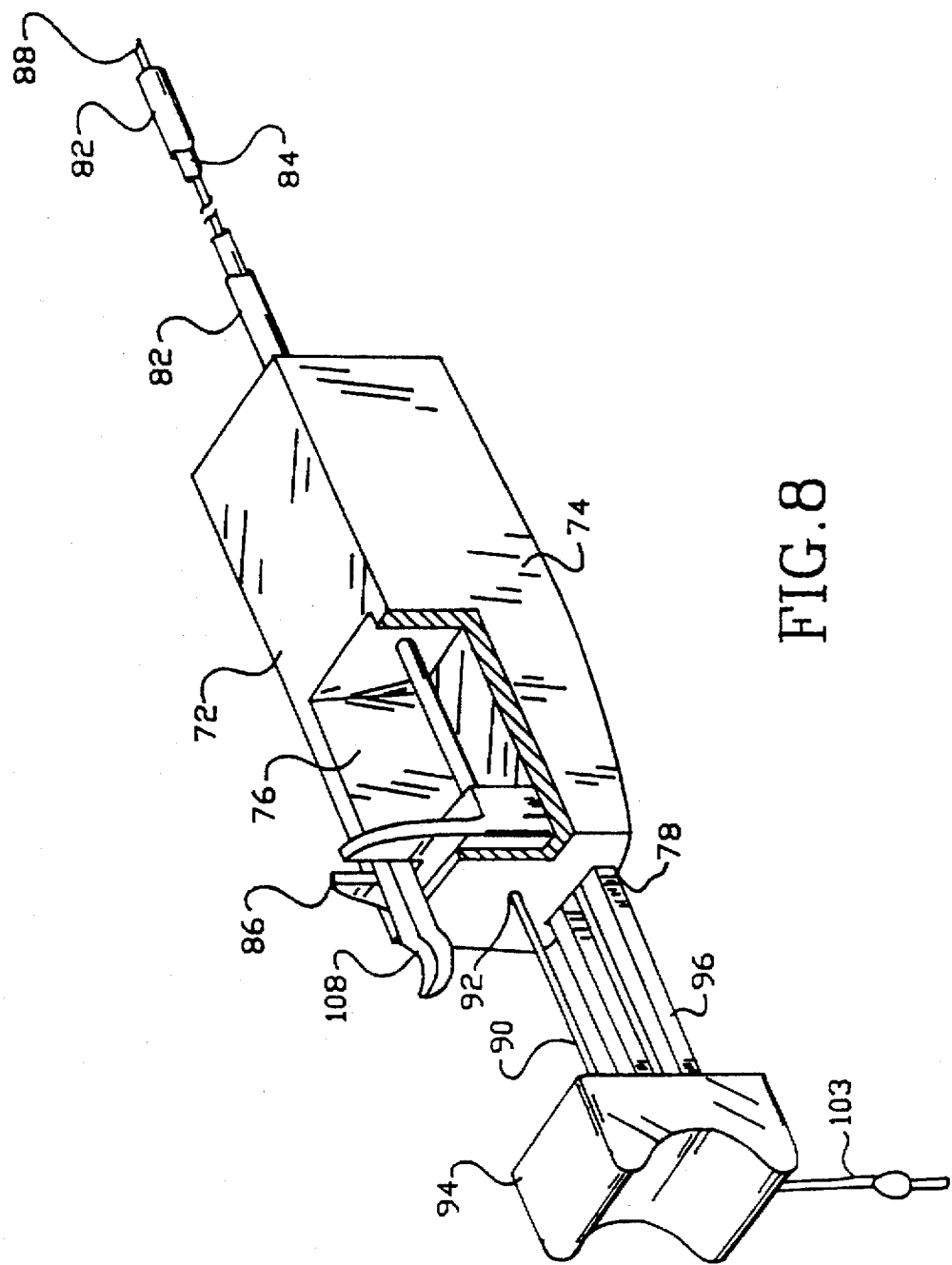
FIG. 8 is a prospective view of one embodiment of this invention having cut away parts to illustrate the construction thereof.
Figure 9:
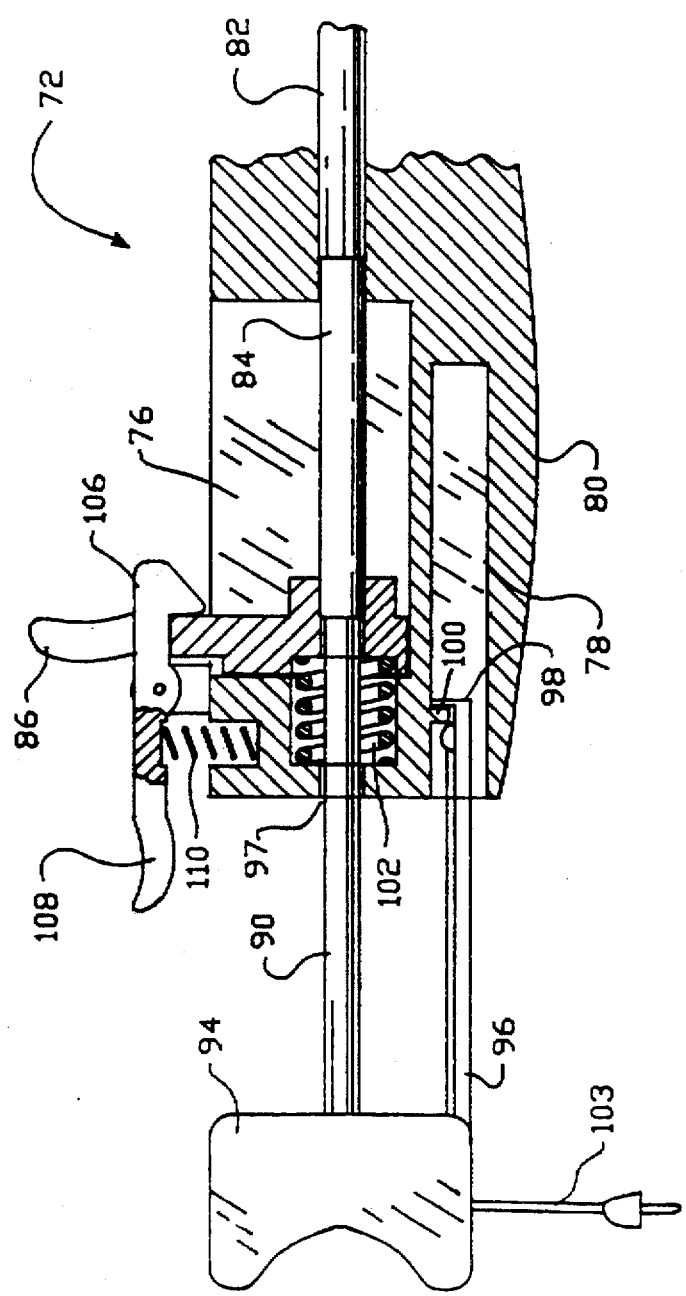
FIG. 9 is a partial cross-sectional view of the embodiment of FIG. 8 in which the stylet is spring-loaded in its retracted position.
Figure 10:
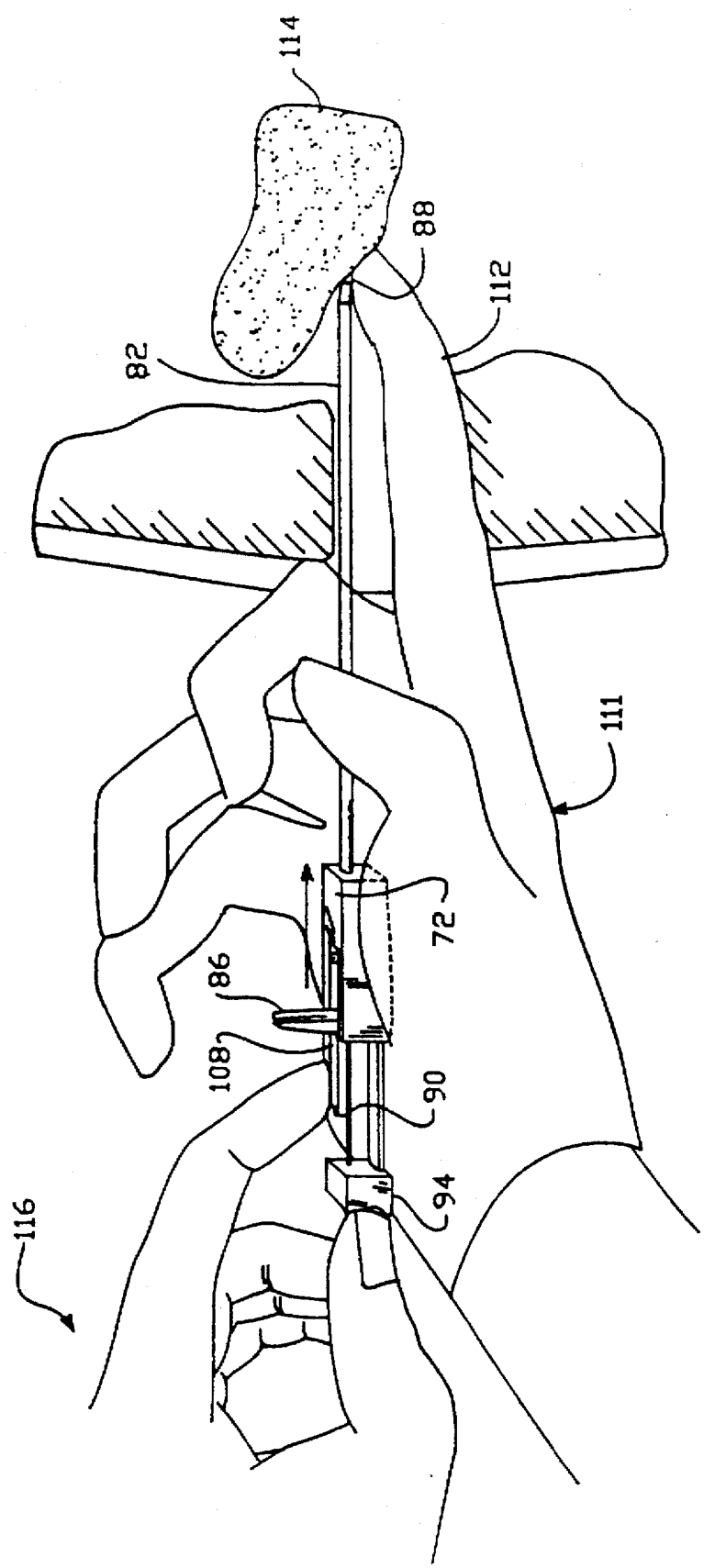
FIG. 10 is a view of the use of the embodiment of FIG. 8 in which the physician has guided the guide tube and stylet point to a desired location in a gland such as the prostate gland.

FIG. 8 is a prospective view of one transrectal embodiment of this invention having cut away parts to illustrate the construction thereof, and FIG. 9 is a partial cross-section of the handle of the embodiment of FIG. 8 wherein the cutting cannula is spring-loaded in its retracted position. Although the description hereinbelow may make reference to certain materials and constructions, it will be obvious to those of skill in the art to adapt other materials and arrangements of the elements, and the illustrations are for exemplary purposes only. It is preferred to utilize a handle 72 formed from plastic, such as polystyrene, and designed for the needle to be disposable after use. Handle 72 preferably includes a curved bottom portion 74 which will fit comfortably in the physician's palm. A recess or slot 76 is provided in the rear portion of handle 72 as well as a slot 76 adjacent the bottom surface 80. A guide tube 82 is disposed in the forward end of handle 72 and is cemented or otherwise anchored therein. Guide tube 82 may be of any suitable material, such as stainless steel, and may have a projecting length on the order of 11 to 16 cm and an outside diameter of about 2 mm. Slidably disposed within guide tube 82 is cutting cannula 84 having a diameter of about 1.5 mm and an overall length of about 15 to 20 cm. The proximal end of cannula 84 is provided with a thumb tab 86 attached thereto. Thumb tab 86 is configured to fit recess 76 and to be able to slide from the rear position shown to a forward position. The amount of movement will depend upon the distance to the tissue to be ablated.

A stylet 88, which may have a length of about 19 to 24 cm and a diameter of about 1 mm, is telescopically disposed within cannula 84 and is attached to control rod 90 extending through opening 92 in the rear wall end of body 72. A push knob 94 is attached to the proximal end of control rod 90 and is moveable forward to contact the rear wall of body 72. A movement forward of about 2.5 cm is suitable. A stop bar 96 provided with a catch portion 98 is connected to push knob 94. Stopbar 96 is shown in the full rearward position in which catch 98 has engaged tab 100 in recess 78. Preferably, knob 94 and stopbar 96 are formed from plastic which has sufficient flexibility to cause catch 98 to disengage when a slight forward pressure is placed on push knob 94. With both stylet 88 and cannula 84 in their fully retracted positions, the distal end of cannula 94 does not extend beyond the distal end of guide tube 82 while the tip of stylet 88 extends slightly beyond the distal end of guide tube 82.

The cannula 84, when in the retracted position, is spring-loaded by means of coil spring 102 in recess 104 at the rear portion of handle 78. Spring 102 is maintained in the compressed condition by detent lever 106 working against coil spring 110. As will be readily understood, at the point at which the physician desires to move cannula 84 forward, he pushes down on release tab 108, permitting spring 102 to snap thumb tab 86 fully forward.

The stylet is connected to a source of RF energy by conventional connections, for example the power connector 103.

FIG. 19 is a view of the use of the embodiment of FIGS. 8 and 9 in which the physician has guided the guide tube and stylet point to a desired location in a gland such as the prostate gland. The physician places the handle 72 in the right hand 111 with thumb tab 86 projecting outward. The tip of the index finger 112 i is placed at the distal end of guide tube 82 which is in the condition with stylet 88 and cannula 84 (FIG. 9) fully retracted. The physician permits the tip of style 88 to be forced against the fingertip. Using the right hand only, he inserts the index finger 112 and guide tube 82 into the patient's rectum and contacts the prostate gland 114 with the fingertip. The physician may the explore the surface of the gland to find a portion to be ablated. At that point, he may force the sharpened tip of the cannula 84 into the prostate. Next, the physician, using the left hand 116, depresses release tab 108, releasing the thumb tab 86 and projecting the stylet 88 into the prostate tissue.

To those skilled in the art to which this invention relates, many changes in construction and widely differing embodiments and applications will make themselves known without departing from the spirit and scope of the invention. The disclosure and the description herein are purely illustrative and are not intended to be in any sense limiting.

We claim:

1. A method of medical treatment of the prostate, comprising:

providing an ablation apparatus including a cannula, an electrode at least partially positioned in the cannula, and an insulation sleeve positioned in a surrounding relationship to at least a portion of the electrode;

positioning a distal end of the cannula in a rectum of a patient;

advancing the distal end of the cannula through a rectal wall of the rectum;

advancing a distal end of the electrode from the cannula into the prostate;

delivering electromagnetic energy from the electrode to the prostate; and creating an ablation zone in the prostate.

2. The method of claim 1, wherein the electrode and insulation sleeve are advanced into the prostate.

3. The method of claim 2, wherein a position of the insulation sleeve is adjusted after the electrode and insulation sleeve have been advanced into the prostate.

4. The method of claim 2, wherein a distal end of the insulation sleeve is advanced in a direction away from a distal end of the electrode after the electrode and insulation sleeve are advanced into the prostate.

5. The method of claim 1, wherein the cannula has a sharpened distal end.

6. The method of claim 1, wherein the electrode is electromagnetically coupled to an RF energy source.

7. The method of claim 1, wherein the electrode has at least a section made of a shaped memory metal.

8. The method of claim 1, wherein a distal end of the electrode is made of a shaped memory metal.

9. The method of claim 1, wherein the ablation apparatus further comprises:

a visualization scope.

10. A method of medical treatment of the prostate, comprising:

providing an ablation apparatus including a cannula, a stylet and an electrode at least partially positioned in the stylet, and an insulation sleeve positioned in a surrounding relationship to at least a portion of the electrode;

positioning a distal end of the cannula in a rectum of a patient;

advancing a distal end of the stylet through a rectal wall of the rectum;

advancing a distal end of the electrode from the stylet into the prostate;

deliverying electromagnetic energy from the electrode to the prostate; and creating an ablation zone in the prostate.

11. The method of claim 10, wherein the electrode and insulation sleeve are advanced into the prostate.

12. The method of claim 11, wherein a position of the insulation sleeve is adjusted after the electrode and insulation sleeve have been advanced into the prostate.

13. The method of claim 11, wherein a distal end of the insulation sleeve is advanced in a direction away from a distal end of the electrode after the electrode and insulation sleeve are advanced into the prostate.

14. The method of claim 10, wherein the cannula has a sharpened distal end.

15. The method of claim 10, wherein the stylet has a sharpened distal end.

16. The method of claim 10, wherein the electrode is electromagnetically coupled to an RF energy source.

17. The method of claim 10, wherein the electrode has at least a section made of a shaped memory metal.

18. The method of claim 10, wherein a distal end of the electrode is made of a shaped memory metal.

19. The method of claim 10, wherein the ablation apparatus further comprises:

a visualization scope.

* * * * *